(12) United States Patent
Wang et al.

(10) Patent No.: US 9,931,081 B2
(45) Date of Patent: Apr. 3, 2018

(54) APPARATUS AND METHOD FOR ECG MOTION ARTIFACT REMOVAL

(71) Applicant: KONINKLIJKE PHILIPS N.V., Eindhoven (NL)

(72) Inventors: Jin Wang, Shanghai (CN); Dan Zhao, Shanghai (CN); Cheng Shi, Shanghai (CN); Wei Li, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 150 days.

(21) Appl. No.: 14/780,825

(22) PCT Filed: Mar. 17, 2014

(86) PCT No.: PCT/IB2014/059876
§ 371 (c)(1),
(2) Date: Sep. 28, 2015

(87) PCT Pub. No.: WO2014/155230
PCT Pub. Date: Oct. 2, 2014

(65) Prior Publication Data
US 2016/0058386 A1  Mar. 3, 2016

(30) Foreign Application Priority Data
Mar. 29, 2013 (WO) ............... PCT/CN2013/073483

(51) Int. Cl.
*A61B 5/04* (2006.01)
*A61B 5/00* (2006.01)
*A61B 5/0402* (2006.01)

(52) U.S. Cl.
CPC .......... *A61B 5/7214* (2013.01); *A61B 5/0402* (2013.01); *A61B 5/04017* (2013.01); *A61B 5/721* (2013.01); *A61B 5/725* (2013.01)

(58) Field of Classification Search
CPC . A61B 5/7214; A61B 5/04017; A61B 5/0402; A61B 5/721; A61B 5/725
See application file for complete search history.

(56) References Cited

U.S. PATENT DOCUMENTS 5,521,851 A    5/1996  Wei et al.
5,704,365 A *  1/1998  Albrecht .............. A61B 5/0408
                                                      128/901
(Continued)

FOREIGN PATENT DOCUMENTS

WO    2012103585 A1    8/2012

OTHER PUBLICATIONS

Han et al: "Accelerometer Based Motion Noise Analysis of ECG Signal"; O. Dossel and W.C. Schlegel (EDS); WC 2009, IFMBE Proceedings 25/V, pp. 198-201, 2009.
(Continued)

*Primary Examiner* — Michael Carey
*Assistant Examiner* — Natasha Patel

(57) ABSTRACT

The invention proposes an apparatus for reducing motion artifact in an ECG signal of a patient. The apparatus comprises a calculating unit configured to calculate a mean value beat from the ECG signal; a first obtaining unit configured to obtain a residual signal based on the ECG signal and the mean value beat calculated from the ECG signal; a filtering unit configured to perform filtering of the residual signal with one or more cut off frequencies; a second obtaining unit configured to obtain a modified ECG signal based on the filtered residual signal and the mean value beat; and a determining unit configured to determine the one or more cut off frequencies of the filtering based on an acceleration signal representative of motion status of the patient. By using the proposed apparatus, motion artifacts can be greatly
(Continued)

removed from the ECG signal and the quality of the ECG signal can be therefore improved.

14 Claims, 2 Drawing Sheets

(56) References Cited

U.S. PATENT DOCUMENTS

| | | | |
|---|---|---|---|
| 5,908,393 | A | 6/1999 | Albrecht et al. |
| 6,216,031 | B1 | 4/2001 | Findeis et al. |
| 6,850,796 | B1 | 2/2005 | Mortara |
| 2007/0156190 | A1 | 7/2007 | Cinbis |
| 2008/0183093 | A1* | 7/2008 | Duann ............... A61B 5/04525 600/516 |
| 2011/0066041 | A1* | 3/2011 | Pandia ............... A61B 5/113 600/484 |
| 2011/0257554 | A1* | 10/2011 | Banet ............... A61B 5/0809 600/536 |

OTHER PUBLICATIONS

Kaiser et al: "Artifact Processing During Exercise Testing"; Journal of Electrocardiology, vol. 32, Supplement 1999. pp. 212-219.

Kim et al: "Optimized Adaptive Filter-Set for Wearable Wireless ECG System"; 2011 6th Conference on Computer Sciences and Convergence Information Technology (ICCIT), Dec. 2011, pp. 107-109.

Lui: "Motion Artifact Reduction in Electrocardiogram Using Adaptive Filter"; Journal of Medical and Biological Engineering, vol. 31, No. 1, Jan. 1, 2011, pp. 67-72.

Milanesi et al: "Multichannel Techniques for Motion Artifacts Removal From Electrocardiographic Signals"; Proceedings ot the 28th IEEE EMBS Annual International Conference, New York City, Aug. 30-Sep. 3, 2006, pp. 3391-3394.

Milanesi et al: "Independent Component Analysis Applied to the Removal of Motion Artifacts From Electrocardiographic Signals"; Medical Biol Eng Comput (2008), vol. 46, pp. 251-261.

Tong et al: "Adaptive Reduction of Motion Artifact in the Electrocardiogram"; Proceedings of the Second Joint EMBS/BMES Conference, Houston, Texasd, Oct. 2002, pp. 1403-1404.

Valtino et al: "Comparing Stress ECG Enhancement Algorithms:With an Introduction to a Filter Bank Based Approach"; IEEE Engineering in Medicine and Biology, May/Jun. 1996, vol. 15, No. 3, pp. 37-44.

Wu et al: "An Algorithm for Evaluating the Performance of Adaptive Filters for the Removal of Artifacts in ECG Signals"; IEEE Conadian Conference on Electrical and Computer Engineering, Apr. 2007, pp. 864-867.

Yoon et al: "Adaptive Motion Artifacts Reduction Using 3-Axis Accelerometer in E-Textile ECG Measaurement System"; Journal of Medical Systems, vol. 32, No. 2 (2008), pp. 101-106.

* cited by examiner

APPARATUS AND METHOD FOR ECG MOTION ARTIFACT REMOVAL

CROSS-REFERENCE TO PRIOR APPLICATIONS

This application is the U.S. National Phase application under 35 U.S.C. § 371 of International Application No. PCT/IB2014/059876, filed on Mar. 17, 2014, which claims the benefit of European Patent Application No.PCT/CN2013/073483, filed on Mar. 29, 2013. These applications are hereby incorporated by reference herein.

FIELD OF THE INVENTION

The invention relates to motion artifact removal technique for processing physiological signals, and more particularly, to method and apparatus for reducing ECG signals motion artifact due to patient movement or exercise.

BACKGROUND OF THE INVENTION

ECG (electrocardiogram) signal is obtained from the body of a patient using electrode attached to the body surface. Due to the changes in the electrode-skin impedance caused by movement of the patient, motion artifacts are introduced to the ECG signal.

As disclosed in the publication under the title of "Motion Artifact Reduction in Electrocardiogram Using Adaptive Filter", a portable ECG recorder which uses a triaxial accelerometer to detect the subject's movement is proposed, and the triaxial acceleration signals are used as reference signal for the adaptive filter to cancel the motion artifact.

SUMMARY OF THE INVENTION

The present invention aims to improve the quality, such as signal to noise ratio (SNR) or signal to noise plus interference ratio (SINR), of the ECG signal. More specifically, it aims at reducing motion artifacts in the ECG signal.

In one aspect, an embodiment of the present invention provides an apparatus for reducing motion artifact in an ECG signal of a patient, comprising: a calculating unit configured to calculate a mean value beat from the ECG signal; a first obtaining unit configured to obtain a residual signal based on the ECG signal and the mean value beat calculated from the ECG signal; a filtering unit configured to perform filtering of the residual signal with one or more cut off frequencies; a second obtaining unit configured to obtain a modified ECG signal based on the filtered residual signal and the mean value beat; and a determining unit configured to determine the one or more cut off frequencies of the filtering based on an acceleration signal representative of motion status of the patient.

Motion artifacts caused by the motion of the patient will lead to unacceptable distortion of the ECG signal, and may even lead to diagnostic error.

In order to remove the motion artifacts from the ECG signal, the interference introduced by the motion artifacts is addressed using the acceleration signal representing the motion status of the patient. A correspondence is built up between the cut off frequencies of the filtering and the motion status of the patient.

Thus, it provides the possibility of specifically blocking the frequency components introduced by the motion of the patient. Thereby, the motion artifacts in the ECG signal is reduced and the quality of the ECG signal is improved, which also contributes to the reduction of diagnostic error.

In one embodiment, the one or more cut off frequencies of the filtering comprise a signal frequency of the acceleration signal.

Under certain circumstance, e.g. when the patient is walking or running, the acceleration signal may be considered as a periodic signal. The signal frequency of the acceleration signal is considered to be corresponding to the frequency component that introduces sever interference to the ECG signal. Thus, blocking the signal frequency of the acceleration signal can reduce the motion artifacts in the ECG signal.

In one embodiment, the signal frequency of the acceleration signal could be easily determined according to the time interval between two successive peak values of the acceleration signal.

Since the signal frequency of the acceleration signal could be easily determined without greatly increasing the computational cost, a cost saving implementation of this embodiment is predictable.

In another embodiment, the one or more cut off frequencies of the filtering comprise N frequencies corresponding to top N power energy of the power spectrum of the acceleration signal.

Since the bandwidth of the motion artifacts overlaps with that of the ECG signal especially when the patient is walking or running, it is not possible to remove all the frequency components of the motion artifacts from the ECG signal. However, those skilled in the art shall appreciate that the frequency component having the strongest power energy in the power spectrum of the acceleration signal brings the most sever interference to the ECG signal, thus it is much more practical and meaningful to remove only the frequency components corresponding to top N power energy of the power spectrum of the acceleration signal from the ECG signal.

Advantageously, N is in range of [1, 10]. In one embodiment of the invention, N is 3.

In the embodiment where N is 3, it is expected that most of the motion artifacts can be removed from the ECG signal, and so the achieved quality of the ECG signal could satisfy the requirement thereof in most of the application scenarios.

Advantageously, the apparatus further comprises an adaptive filter configured to perform an adaptive filtering of the ECG signal with the acceleration signal; and the calculating unit is configured to calculate the mean value beat from the adaptive filtered ECG signal; the first obtaining unit is configured to obtain the residual signal based on the adaptive filtered ECG signal and the mean value beat calculated from the adaptive filtered ECG signal.

In other words, the adaptive filter performs an adaptive filtering of the ECG signal using the acceleration signal as reference signal. Thus, part of the motion artifacts can be removed from the ECG signal and there should be less motion artifacts in the filtered ECG signal than in the raw ECG signal. Accordingly, the additional use of the adaptive filter may further improve the quality of the ECG signal.

In another aspect, one embodiment of the present invention provides an apparatus for acquiring an ECG signal of a patient, the apparatus comprising: a first sensing unit for obtaining the ECG signal of a patient; a second sensing unit for obtaining an acceleration signal representative of motion status of the patient and an apparatus for reducing motion artifact in the ECG signal of the patient according to the first aspect of the invention connected with the first sensing unit and the second sensing unit.

In another aspect, one embodiment of the present invention provides a method of reducing motion artifact in an ECG signal of a patient, the method comprising the steps of: calculating a mean value beat from the ECG signal; obtaining a residual signal based on the ECG signal and the mean value beat calculated from the ECG signal; performing filtering of the residual signal with one or more cut off frequencies; obtaining a modified ECG signal based on the filtered residual signal and the mean value beat; and determining the one or more cut off frequencies of the filtering based on an acceleration signal representative of motion status of the patient.

In one embodiment, the step of determining comprises determining a signal frequency of the acceleration signal as the cut off frequency of the filtering, and in another embodiment, the step of determining comprises determining N frequencies corresponding to the top N power energy of the power spectrum of the acceleration signal as the cut off frequencies of the filtering.

DESCRIPTION OF THE DRAWINGS

The above and other objects and features of the present invention will become more apparent from the following detailed description considered in connection with the accompanying drawings, in which.

Throughout the above drawings, like reference numerals will be understood as referring to like, similar or corresponding features or functions.

DETAILED DESCRIPTION

Reference will now be made to embodiments of the invention, one or more examples of which are illustrated in the figures. The embodiments are provided by way of explanation of the invention, and are not meant as a limitation of the invention. For example, features illustrated or described as part of one embodiment may be used with another embodiment to yield still a further embodiment. It is intended that the invention encompasses these and other modifications and variations as come within the scope and spirit of the invention.

Figure 1:
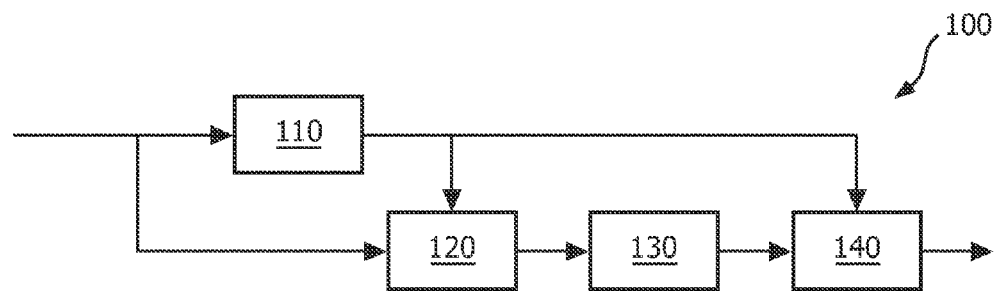
FIG. 1 illustrates a block diagram of an apparatus for reducing motion artifact according to the state of the art.

FIG. 1 illustrates a block diagram of an apparatus for reducing motion artifact according to the state of the art.

Referring to FIG. 1, the apparatus 100 for reducing motion artifact comprises a calculating unit 110, a first obtaining unit 120, a filtering unit 130, and a second obtaining unit 140.

The calculating unit 110 is configured to calculate a mean value beat from the ECG signal.

Specifically, in the calculating unit 110, the mean value beat may be calculated based on averaging of successive ECG cycles. Those skilled in the art may appreciate that other algorithms may be used for the calculating unit 110.

The first obtaining unit 120 is configured to obtain a residual signal based on the ECG signal and the mean value beat calculated from the ECG signal. Thus, the ECG signal and the mean value beat calculated therefrom are provided at the input of the first obtaining unit 120.

Besides, the first obtaining unit 120 may comprise a subtracting unit to subtract the mean value beat from the ECG signal to obtain the residual signal. Those skilled in the art may appreciate that the first obtaining unit 120 may adopt other algorithms to obtain the residual signal. The residual signal obtained at the output of the first obtaining unit 120 is provided as input of the filtering unit 130.

The filtering unit 130 is configured to perform filtering of the residual signal with fixed cut off frequencies. For example, the filtering unit 130 may comprise a low-pass filter to reduce muscle noise and a high-pass filter to reduce baseline wander. Those skilled in the art may appreciate that, the filtering unit 130 may also be considered as a band-pass filter. For example, the band-pass filter may have a bandwidth ranging from 0.05 Hz to 250 Hz. Other cut off frequencies may be adopted for the band-pass filter to restrict the frequency band of the residual signal.

The filtered residual signal obtained at the output of the filtering unit 130 is fed to an input of the second obtaining unit 140. The second obtaining unit 140 is configured to obtain a modified ECG signal based on the filtered residual signal and the mean value beat, thus, the mean value beat calculated from the ECG signal is also provided as an input of the second obtaining unit 140.

Specifically, the second obtaining unit 140 may comprise an adding unit configured to add the filtered residual signal back to the mean value beat to obtain a modified ECG signal. Those skilled in the art may appreciate that the second obtaining unit 140 may adopt other algorithms to obtain the modified ECG signal.

In the existing solutions, both design of mean value beat calculation and design of low-pass/high-pass filter have great influence on the final filtered signal. There are still some noises for the existing solutions, especially in the case of exercise with a fast running speed.

Figure 2:
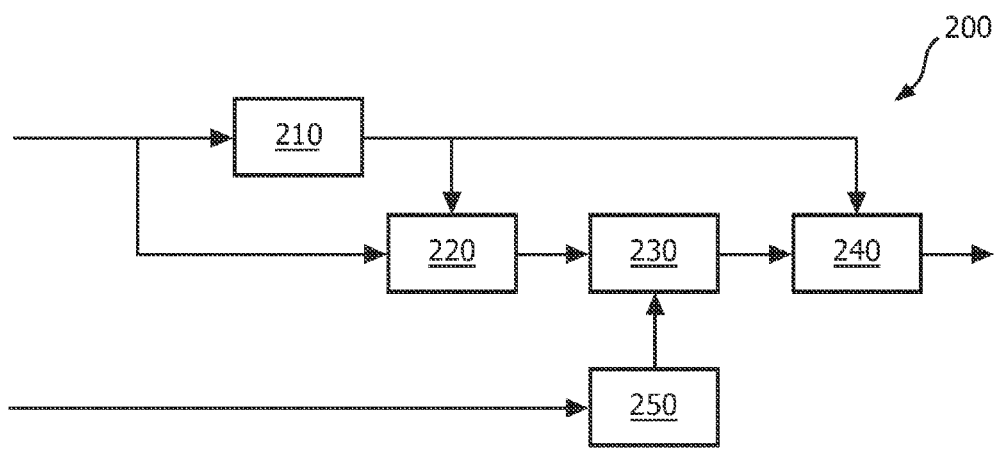
FIG. 2 illustrates a block diagram of an apparatus for reducing motion artifact according to an embodiment of the present invention.

FIG. 2 illustrates a block diagram of an apparatus for reducing motion artifact according to an embodiment of the present invention;

Referring to FIG. 2, the apparatus 200 comprises a calculating unit 210, a first obtaining unit 220, a filtering unit 230, a second obtaining unit 240 and a determining unit 250.

The calculating unit 210, the first obtaining unit 220 and the second obtaining unit 240 are similar to those described in connection with FIG. 1, thus a repeat description of them is omitted.

In the embodiment of the present invention, the one or more cut off frequencies of the filtering unit 230 is determined by the determining unit 250 based on an acceleration signal representative of motion status of the patient.

The acceleration signal may be obtained using an accelerometer sensor placed on the electrode which is attached to the body surface of a patient. An A/D converter may be used to convert the analog acceleration signal of the accelerometer sensor into digital signal. Those skilled in the art may appreciate that, the sampled acceleration signal still represents the motion of the electrode and thus the motion status of the patient.

In one embodiment of the invention, the one or more cut off frequencies determined by the determining unit 250 comprises a signal frequency of the acceleration signal.

Since the acceleration signal represents the motion status of the patient, the signal frequency of the acceleration signal is considered to be corresponding to the frequency component that introduces sever interference to the ECG signal. Using the signal frequency of the acceleration signal as the cut off frequency of the filtering unit 230 specifically reduces the introduced motion artifact.

In one embodiment of the invention, in the determining unit 250, the signal frequency of the acceleration signal could be simply determined according to the time interval between two successive peak values of the acceleration signal. Specifically, the time points of the appearance of the peak values of the acceleration signal are recorded, and the signal frequency of the acceleration signal may be determined based on the time points recorded in succession. Those skilled in the art may appreciate that other methods of determining the signal frequency of the acceleration signal may be adopted.

Those skilled in the art shall appreciate that the part of the frequency components of the acceleration signal may be not overlapped with the frequency spectrum of the ECG signal, and that part of the frequency components could be removed from the ECG signal using various methods of the art. In the following description of the embodiments, the proposed apparatus concentrates on removing the frequency components of the acceleration signal that are overlapped with the spectrum of the ECG signal.

Advantageously, the determining unit 250 determines the signal frequency of the acceleration signal as the cut off frequency of the filtering, only when the determined signal frequency of the acceleration signal is within a predetermined range. For example, the predetermined range may be 0.5 Hz-5 Hz, which is corresponding to a heart rate of 30-300 beats/min. Since the frequency components of the acceleration signal within this range are completely overlapped with the spectrum of the ECG signal, it is difficult to remove them using approach of the art. On the contrary, since the cut off frequency of the filtering is determined on a non-linear basis, the proposed apparatus shows advantage in reducing the motion artifacts introduced by the movement of the patient.

The filtering unit 230 may comprises a band-stop filter, the cut off frequency of which is determined by the determining unit 250, so as to specifically block the signal frequency of the acceleration signal. The filter may be finite impulse response (FIR) filter with the advantage that the delay of the filtered residual signal is constant and signal independent.

Operation of the apparatus according to the invention will be described below in connection with specific example which shall not be considered as limitation on the scope of the invention.

The application scenario is given as: the patient is walking with a step length of 0.6 m and a walking speed of 2.16 km/h, i.e. the stride frequency is 1 Hz.

In the determining unit 250, the signal frequency of the acceleration signal may be determined as 1 Hz which is corresponding to the stride frequency. The determining unit 250 determines the cut off frequency of the filtering unit 230 as 1 Hz, since it is within the predetermined range.

The filtering unit 230 is configured to block the frequency component of 1 Hz, so as to specifically block the frequency component corresponding to the stride frequency.

In another embodiment of the invention, the filtering unit 230 further comprises the low pass filter for reducing muscle noise and the high pass filter for reducing baseline wander described above in connection with FIG. 1. Alternatively, the combination of the low pass filter and the high pass filter can be replaced by a single band pass filter for reducing both muscle noise and other artifacts. For example, a band pass filter having a bandwidth ranging from 0.05 Hz to 250 Hz can be adopted. Those skilled in the art shall appreciate that, the specific bandwidth of the band-pass filter is described here only for illustrative purpose, and other range of the bandwidth may be used and should be considered as within the scope of the invention defined in the claims.

In another embodiment, in the filtering unit 230, the band-stop filter may be combined with the filter(s) for reducing muscle noise and other artifacts. Those skilled in the art may understand that, for the above described application scenario, the filtering unit 230 may be considered as two band-pass filter. Specifically, the filtering unit 230 may be expressed as:

$$\text{Filter} = \begin{Bmatrix} FIR1, & 0.05 \text{ Hz} < \text{bandwidth} < 1 \text{ Hz} \\ FIR2, & 1 \text{ Hz} < \text{bandwidth} < 250 \text{ Hz} \end{Bmatrix}.$$

In another embodiment of the invention, the one or more cut off frequencies determined by the determining unit 250 comprises N frequencies corresponding to top N power energy of the power spectrum of the acceleration signal.

Since the bandwidth of the motion artifacts overlaps with that of the ECG signal when the patient is walking or running, it is not possible to remove all the frequency components of the motion artifacts from the ECG signal. However, those skilled in the art shall appreciate that the frequency component having the strongest power energy in the power spectrum of the acceleration signal brings the most sever interference to the ECG signal, thus it is much more practical and meaningful to remove only the frequency components corresponding to top N power energy of the power spectrum of the acceleration signal from the ECG signal.

Advantageously, N is in range of [1, 10]. In one embodiment of the invention, N is 3. In the following, the present invention will be described in connection with the embodiment where N is 3.

Power spectrum of the acceleration signal could be obtained by applying FFT transformation on the sampled acceleration signal. Those skilled in the art shall appreciate that other approach may be applied to obtain the power spectrum of the acceleration signal. The concrete computation of the power spectrum will not be further described here.

The determining unit 250 may determine 3 frequencies corresponding to the frequency components having the top three FFT amplitudes of the acceleration signal. For example, $f_0$ is the frequency having the greatest power energy, $f_1$ is the frequency having the second greatest power energy, and $f_2$ is the frequency having the third greatest power energy of the power spectrum of the acceleration signal. The footnote index is used to identify the ranking of the power energy of the frequency component in the power spectrum, and it doesn't represent the ranking of the value of the frequency. For example, in one embodiment, the relation among $f_0$, $f_1$, and $f_2$ may read: $f_1 < f_0 < f_2$.

The filtering unit 230 is configured to block those frequencies, i.e. $f_0$, $f_1$ and $f_2$. Those skilled in the art may appreciate that, the filtering unit 230 may be considered as comprising 3 band-pass filters. In this embodiment, the filters are FIR filters. Specifically, the filtering unit 230 may be expressed as:

$$\text{Filter} = \begin{Bmatrix} FIR1, & 0 \text{ Hz} < \text{bandwidth} < f_1 \\ FIR2, & f_1 < \text{bandwidth} < f_0 \\ FIR3, & f_0 < \text{bandwidth} < f_2 \end{Bmatrix}$$

In another embodiment, the filtering unit 230 may be combined with the filter(s) having the bandwidth for reducing muscle noise and baseline wander described above in connection with FIG. 1. Assuming 0.05 Hz$<f_1<f_0<f_2<$250 Hz , the filtering unit 230 may be considered as comprising 4 band-pass filters defined as below:

$$\text{Filter} = \begin{Bmatrix} FIR1, & 0.05 \text{ Hz} < \text{bandwidth} < f_1 \\ FIR2, & f_1 < \text{bandwidth} < f_0 \\ FIR3, & f_0 < \text{bandwidth} < f_2 \\ FIR4, & f_2 < \text{bandwidth} < 250 \text{ Hz} \end{Bmatrix}.$$

Figure 3:
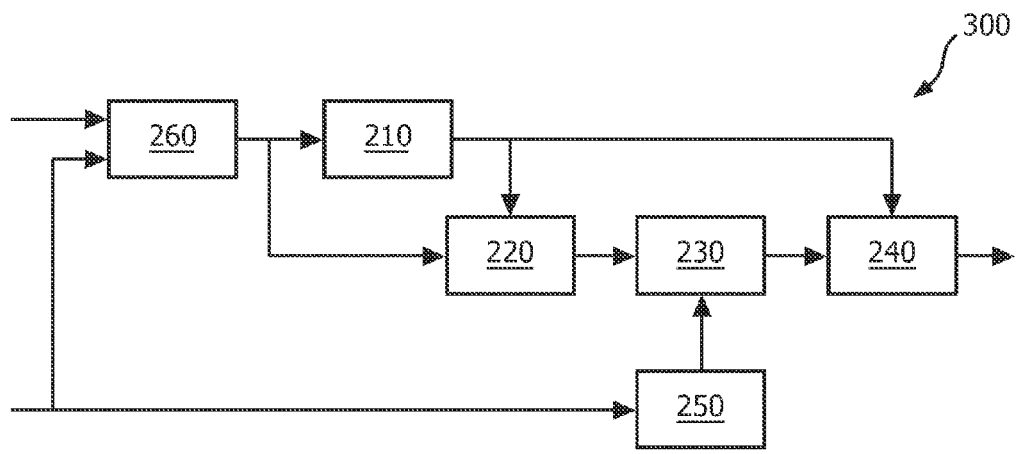
FIG. 3 illustrates a block diagram of an apparatus for reducing motion artifact according to another embodiment of the present invention.

FIG. 3 illustrates a block diagram of an apparatus for reducing motion artifact according to another embodiment of the present invention.

As shown in FIG 3, the apparatus 300 comprises a calculating unit 210, a first obtaining unit 220, a filtering unit 230, a second obtaining unit 240, a determining unit 250 and an adaptive filter 260.

The calculating unit 210, the first obtaining unit 220, the filtering unit 230, the second obtaining unit 240 and the determining unit 250 are similar to those described in connection with FIG. 2. The difference between the embodiments shown in FIG. 2 and FIG. 3 lies in the fact that in FIG. 3 the adaptive filtered ECGs signal is used instead of raw ECG signal as input signal for the calculating unit 210 and the first obtaining unit 220.

The adaptive filter 260 is configured to perform an adaptive filtering of the ECG signal with the acceleration signal. The adaptive filter 260 may be recursive least square (RLS) filter, least mean square (LMS) filter or other filters that would come to those skilled in the art.

Using the acceleration signal as reference signal, the adaptive filter 260 performs an adaptive filtering of the ECG signal. Thus part of the motion artifacts in the ECG signal can be removed.

In the embodiment shown in FIG. 3, the calculating unit 210 is configured to calculate the mean value beat from the adaptive filtered ECG signal, and the first obtaining unit 220 is configured to obtain the residual signal based on the adaptive filtered ECG signal and the mean value beat calculated from the adaptive filtered ECG signal.

Using the filtered ECG signal instead of the raw ECG signal in the embodiment of the invention could further reduce the motion artifacts in the ECG signal and improve the quality of the ECG signal.

Those skilled in the art may appreciate that, the apparatus for reducing motion artifact according to the invention may be implemented by FPGA, CPU, DSP unit or any other means.

Figure 4:
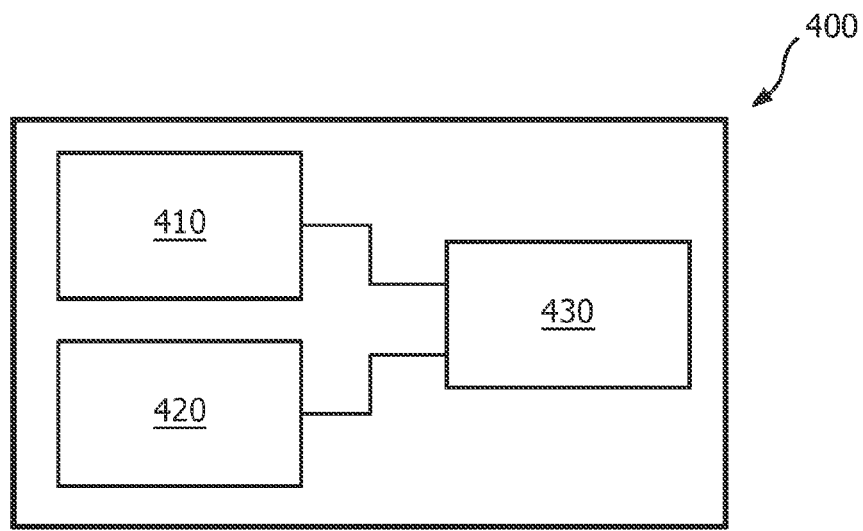
FIG. 4 illustrates a block diagram of an apparatus for acquiring an ECG signal according to one embodiment of the invention.

In another aspect, one embodiment of the invention further provides an apparatus for acquiring an ECG signal of a patient. FIG. 4 shows a block diagram of the apparatus for acquiring an ECG signal according to one embodiment of the invention.

As shown in FIG. 4, the apparatus 400 for acquiring an ECG signal comprises a first sensing unit 410, a second sensing unit 420, and an apparatus 430.

The first sensing unit 410 is configured to obtain the ECG signal of a patient. In one embodiment of the invention, the first sensing unit 410 is implemented as several electrodes. In operation, these electrodes are attached to the body surface of a patient. Special agent may be used between the electrodes and the body surface to improve the quality of the acquired ECG signal.

Those skilled in the art may appreciate that, the first sensing unit 410 further comprises a signal conditioning circuit to prepare the ECG signal for the latter processing. An A/D converter and a filter may be comprised in the signal conditioning circuit. Those skilled in the art may appreciate that other implementations of the first sensing unit 410 are also possible.

The second sensing unit 420 is configured to obtain the acceleration signal. In one embodiment of the invention, the second sensing unit 420 is implemented as an accelerometer sensor placed on the first sensing unit or individually attached to the body surface of the patient.

Those skilled in the art may appreciate that the second sensing unit 420 may also comprise a signal conditioning circuit to deal with the obtained acceleration signal. The signal conditioning circuit in the second sensing unit 420 is similar to that in the first sensing unit 410. Other implementations of the second sensing unit 420 may be adopted.

The apparatus 430 is connected with the first sensing unit 410 and the second sensing unit 420 to receive the ECG signal and the acceleration signal as input. The apparatus 430 is configured according to the first aspect of the invention mentioned above to reduce the motion artifact in the ECG signal of the patient.

Those skilled in the art may appreciate that the apparatus 400 can be a portable ECG recorder.

In another aspect, one embodiment of the invention further provides a method of reducing motion artifact in an ECG signal of a patient. FIG. 4 shows a flow chart of a method of reducing motion artifact.

Figure 5:
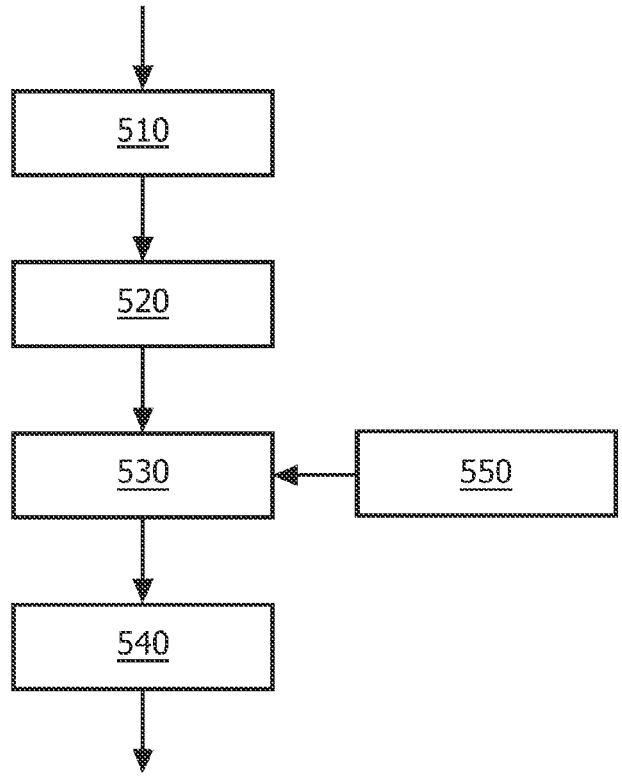
FIG. 5 illustrates a flow chart of the method of reducing motion artifact in an ECG signal of a patient according to one embodiment of the present invention.

As shown in FIG. 5, the method comprises the steps of S510, S520, S530, S540, and S550.

In the step S510, a mean value beat is calculated from the ECG signal.

In the step S520, a residual signal is obtained based on the ECG signal and the mean value beat calculated from the ECG signal.

In the step S530, filtering of the residual signal is performed with one or more cut off frequencies.

In the step S540, a modified ECG signal is obtained based on the filtered residual signal and the mean value beat.

In the step S550, the one or more cut off frequencies of the filtering are determined based on an acceleration signal representative of motion status of the patient.

Using the proposed method, it is possible to specifically block the frequency components corresponding to the motion artifacts introduced by the motion of the patient. Thus, the motion artifacts in the ECG signal is reduced and the quality of the ECG signal is improved, which also contributes to the reduction of diagnostic error.

In one embodiment of the invention, the step S550 may further comprise determining the signal frequency of the acceleration signal as the cut off frequency of the filtering.

In one embodiment of the invention, the step S550 further comprises determining the signal frequency of the acceleration signal according to the time interval between two successive peak values of the acceleration signal.

In another embodiment of the invention, the step S550 further comprises determining N frequencies corresponding to top N power energy of the power spectrum of the acceleration signal as the cut off frequencies of the filtering.

Advantageously, prior to the step S510, the method further comprises a step of performing an adaptive filtering of the ECG signal with the acceleration signal. Then, in the step S510, the mean value beat is calculated from the adaptive filtered ECG signal, and in the step S520, the residual signal is obtained based on the adaptive filtered ECG signal and the mean value beat calculated from the adaptive filtered ECG signal.

The additional use of the adaptive filter may further improve the quality of the ECG signal.

A set of computer-executable instructions is further proposed to perform the methods described above. The instructions can reside in the calculating unit 210, the first obtaining unit 220, the filtering unit 230, and the second obtaining unit 240, the determining unit 250 and the adaptive filter 260, to perform any step of the above disclosed methods.

Although the present invention will be described with reference to the embodiment shown in the drawings, it should be understood that the present invention may be embodied in many alternate forms including any combination of hardware and software. In addition, any suitable size, shape or type of materials, elements, computer program elements, computer program codes, or computer program modules could be used.

While discussed in the context of computer program code, it should be understood that the modules may be implemented in hardware circuitry, computer program code, or any combination of hardware circuitry and computer program code.

It should be noted that the above described embodiments are given for describing rather than limiting the invention, and it is to be understood that modifications and variations may be resorted to without departing from the spirit and scope of the invention as those skilled in the art readily understand. Such modifications and variations are considered to be within the scope of the invention and the appended claims. The protection scope of the invention is defined by the accompanying claims. In addition, any of the reference numerals in the claims should not be interpreted as a limitation to the claims. Use of the verb "comprise" and its conjugations does not exclude the presence of elements or steps other than those stated in a claim. The indefinite article "a" or "an" preceding an element or step does not exclude the presence of a plurality of such elements or steps.

The invention claimed is:

1. An apparatus for reducing motion artifact in an ECG signal obtained from a patient, the apparatus comprising:
   a calculating unit configured to receive the ECG signal and to calculate a mean value beat from the ECG signal;
   a first obtaining unit configured to obtain a residual signal based on the ECG signal and the mean value beat calculated from the ECG signal;
   a filtering unit configured to perform filtering of the residual signal with one or more cut off frequencies;
   a second obtaining unit configured to obtain a modified ECG signal using the filtered residual signal and the mean value beat; and
   a determining unit configured to determine the one or more cut off frequencies of the filtering unit for filtering the residual signal using an acceleration signal representative of motion status of the patient.

2. The apparatus of claim 1, wherein the one or more cut off frequencies of the filtering comprise a signal frequency of the acceleration signal.

3. The apparatus of claim 2, wherein the signal frequency of the acceleration signal is determined according to a time interval between two successive peak values of the acceleration signal.

4. The apparatus of claim 1, wherein the one or more cut off frequencies of the filtering comprise N frequencies corresponding to top N power energy of a power spectrum of the acceleration signal.

5. The apparatus of claim 4, wherein N is in range of [1, 10].

6. The apparatus of claim 5, wherein N is 3.

7. The apparatus of claim 1, further comprising:
   an adaptive filter configured to perform an adaptive filtering of the ECG signal using the acceleration signal as a reference signal,
   wherein the calculating unit is configured to receive the adaptive filtered ECG signal as the ECG signal and to calculate the mean value beat from the adaptive filtered ECG signal, and
   wherein the first obtaining unit is configured to obtain the residual signal based on the adaptive filtered ECG signal as the ECG signal and the mean value beat calculated from the adaptive filtered ECG signal.

8. The apparatus of claim 1, wherein the first obtaining unit comprises:
   a subtracting unit configured to subtract the mean value beat from the ECG signal to obtain the residual signal.

9. The apparatus of claim 1, wherein the second obtaining unit comprises:
   an adding unit configured to add the filtered residual signal back to the mean value beat to obtain the modified ECG signal.

10. A method of reducing motion artifact in an ECG signal obtained from a patient, the method comprising:
    receiving the ECG signal obtained from an ECG signal sensor;
    calculating a mean value beat from the ECG signal using a processor;
    obtaining a residual signal based on the ECG signal and the mean value beat calculated from the ECG signal;
    receiving an acceleration signal representative of motion status of the patient obtained from an acceleration sensor;
    determining, using the processor, one or more cut off frequencies of a filtering unit using the acceleration signal;
    filtering the residual signal using the filtering unit with one or more cut off frequencies; and
    obtaining, using the processor, a modified ECG signal using the filtered residual signal and the mean value beat.

11. The method of claim 10, wherein determining the one or more cut off frequencies comprises:
    determining a signal frequency of the acceleration signal using the signal frequency as the cut off frequency of the filtering.

12. The method of claim 11, wherein
    the signal frequency of the acceleration signal is determined according to a time interval between two successive peak values of the acceleration signal.

13. The method of claim 10, wherein determining the one or more cut off frequencies comprises:
    determining N frequencies corresponding to top N power energy of a power spectrum of the acceleration signal as the cut off frequencies of the filtering.

14. The method of claim 10, further comprising:
adaptive filtering of the ECG signal with the acceleration signal as a reference signal, prior to calculating the mean value beat,
wherein the mean value beat is calculated from the adaptive filtered ECG signal, and
wherein the residual signal is obtained based on the adaptive filtered ECG signal and the mean value beat calculated from the adaptive filtered ECG signal.

* * * * *